United States Patent [19]

Osterholm

[11] Patent Number: 4,532,591
[45] Date of Patent: Jul. 30, 1985

[54] METHOD AND APPARATUS FOR TOMOGRAPHIC DIAGNOSIS

[75] Inventor: Jewell L. Osterholm, Radnor, Pa.

[73] Assignee: Thomas Jefferson University, Philadelphia, Pa.

[21] Appl. No.: 404,898

[22] Filed: Aug. 3, 1982

[51] Int. Cl.³ ............................................ G06F 15/42
[52] U.S. Cl. ..................................... 364/414; 378/901; 378/6; 378/11; 378/25; 358/111
[58] Field of Search ................ 364/414, 415; 378/901, 378/4, 21, 6, 11, 25; 358/111; 128/731

[56] References Cited

U.S. PATENT DOCUMENTS

| 3,924,129 | 12/1975 | LeMay | 250/336 |
| 4,076,985 | 2/1978 | LeMay | 250/445 |
| 4,157,572 | 6/1979 | Kennedy et al. | 358/111 |
| 4,415,980 | 11/1983 | Buchanan | 378/4 |
| 4,430,749 | 2/1984 | Schardt | 364/414 |
| 4,437,161 | 3/1984 | Anderson | 378/901 |

FOREIGN PATENT DOCUMENTS 495917  4/1977  Australia ............................ 364/414

OTHER PUBLICATIONS

Schriber "Brain Storms", Forbes, Jun. 6, 1983, p. 116.

Primary Examiner—Jerry Smith
Assistant Examiner—Allen MacDonald
Attorney, Agent, or Firm—Woodcock, Washburn, Kurtz, Mackiewicz & Norris

[57] ABSTRACT

A computer-assisted tomographic image is overlayed with the visual indication of any regions representing a deviation from a norm. The overlaid region may indicate a deviation of the radiodensity in that region. The overlaid region may also indicate a deviation from an electrophysiological norm based on compressed spectral analysis of an electroencephalographic signal or evoked potentials represented by such a signal.

10 Claims, 3 Drawing Figures

METHOD AND APPARATUS FOR TOMOGRAPHIC DIAGNOSIS

BACKGROUND OF THE INVENTION

This invention relates to a method and apparatus for generating an enhanced tomogram, more specifically, a method and apparatus providing computer enhancement of a computer-assisted tomogram utilizing, for example, electrophysiological data.

Computer-assisted tomograms commonly referred to by the acronym CAT are currently utilized in diagnosis of the human body with particular emphasis on the central nervous system. CAT scanning units which generate such tomograms rely solely upon minute differences in tissue penetration to radiation as a source of information. During its extremely short life span, the CAT scanning unit has undergone rapid change and improvement such that the latest models have excellent resolution and display.

A parallel yet quite different computer-dependent system which is utilized for diagnosis of the central nervous system relies on electrophysiology. This system delineates the central nervous system functioning by analysis of cerebral activity utilizing an electroencephalogram commonly referred to as an EEG. Computer analysis of an EEG in terms of defining, determining and separating the spectrum of component wave forms of various frequencies and amplitude to develope a compressed spectral array is commonly referred to as CSA. Another technique relying upon evoked potentials is referred to as EPS.

As suggested above, an EEG wave form comprises a highly complex signal including a plurality of components and the EEG is merely a summation of all of these components. CSA is a presentation analysis of the EEG which, through the use of a computer, separates the components within the EEG envelop and displays these components. Standard EEG frequencies of 3-4 Hz. (delta); 4-8 Hz. (theta); and 12-30 Hz. (alpha-beta) are individually analyzed by CSA computation and the wattage in these bands computed. At the clinical level, a conventional EEG might visually appear quite normal yet the CSA display might reveal significant shifts to lower frequencies and thereby demonstrate a clear functional abnormality. In other words, without the CSA, the routine EEG may be a relatively insensitive tool. However, with CSA, the the EEG information can provide a sensitive method of assessing ongoing cerebral electrical activity.

Evoked potentials which are referred to as EPS are developed at cortical levels in response to a specific sensory stimulus. The stimulus may be sensory, auditory or visual. Under the usual conditions, the arrival of repetitive stimuli are buried in the ongoing EEG wave form and cannot be discerned. However, by utilizing computing modalities with time locked stimuli, an evoked response is developed. The evoked response has several components which are described in appearance latency as well as amplitude. This electrophysiologic method actually tests the functional capability of a neurocircuit by evaluating its response to a stimulus.

A CAT scanning unit has several limitations which may result in diagnostic errors. For example, isodense lesions may go undiagnosed since, for example, hematomas of sufficient age may have a radiographic appearance similar to that of the brain. Other diagnostic errors may arise out of metabolic disturbances such as general or local anoxia prior to actual infarction. Still other diagnostic errors arise out of CNS infections, seizures, hypoglycemia or systemic toxins (i.e., uremia, hepatic failure, etc.). In some instances, lesions, either single or multiple may be below CAT scanning resolution which can lead to a faulty diagnosis. Additional diagnostic errors may arise from bilateral lesions without shifting and/or extra-axial lesions such as certain subdural hematomas. In many instances, CAT scanning at a very early point in time after a stroke may be non-diagnostic. In other instances edema of the brain may be difficult to detect utilizing conventional CAT scanning techniques.

In summary, CAT scanning may be less than a perfect diagnostic tool. In no small part, this is due to the human incapability of the physician to detect subtleties in the CAT scan which might provide important diagnostic information.

SUMMARY OF THE INVENTION

It is an overall object of this invention to provide a tomographic method and apparatus with improved diagnostic capabilities.

It is a more specific object of this invention to provide a method and apparatus with improved diagnostic capabilities by combining the diagnostic capabilities of tomography with electrophysiology.

In accordance with these and other objects of the invention, a tomographic imaging apparatus comprises X-ray means for scanning a portion of a body with X-radiation and detecting the X-radiation scanning the body, a processing means for processing detected signals representing the radiodensity of the various regions of the body and imaging means coupled to the processing means for generating an image representing the radiodensity of the various regions of the body.

In further accordance with this invention, signals representing a predetermined condition at various regions of the body are stored in memory and signals representing the actual condition of the body at various regions are detected. The stored signals representing the predetermined condition and the detected signals representing the actual condition are compared and signals representing the deviation of the actual condition from the predetermined condition are generated and stored in memory. A display is responsive to the signal representing the deviation so as to visually indicate on a tomographic image a region representing the deviation of the actual condition of the body from a predetermined condition of the body.

In the preferred embodiment of the invention, the display generates an image of various regions in a plane through the body and a visual overlay of one of the regions in the plane is generated representing the deviation of the actual condition from the predetermined condition in that region.

In the preferred embodiment of the invention, the portion of the body scanned with X-radiation is the central nervous system and an image is generated representing the radiodensity of various regions of the central nervous system. In this embodiment, the signal stored in memory represents a predetermined condition of the central nervous system and signals are detected representing the actual condition of the central nervous system. In one particularly preferred embodiment, signals stored in memory may represent predetermined normal radiodensities of the central nervous system and the signals detected may represent the actual radiodensities of the central nervous system. After comparison, a visual indication is obtained as to the deviation of the actual radiodensity from the predetermined normal radiodensity in one of the regions. In another particularly preferred embodiment of the invention, the signals stored in memory represent a predetermined electrophysiological condition in the central nervous system at various regions thereof and the signals which are detected are the actual electrophysiological condition of the central nervous system. After comparison, the imaging means visually indicates any one of the regions representing a deviation of the actual electrophysiological condition from the predetermined electrophysiological condition. The electrophysiological condition stored in memory and detected may comprise spectrally analyzed components of an electroencephalographic signal or CSA. In the alternative, the electrophysiological condition stored in memory and detected may represent potentials evoked in response to a stimulus or EPS.

DETAILED DESCRIPTION OF PREFERRED EMBODIMENTS

Figure 1:
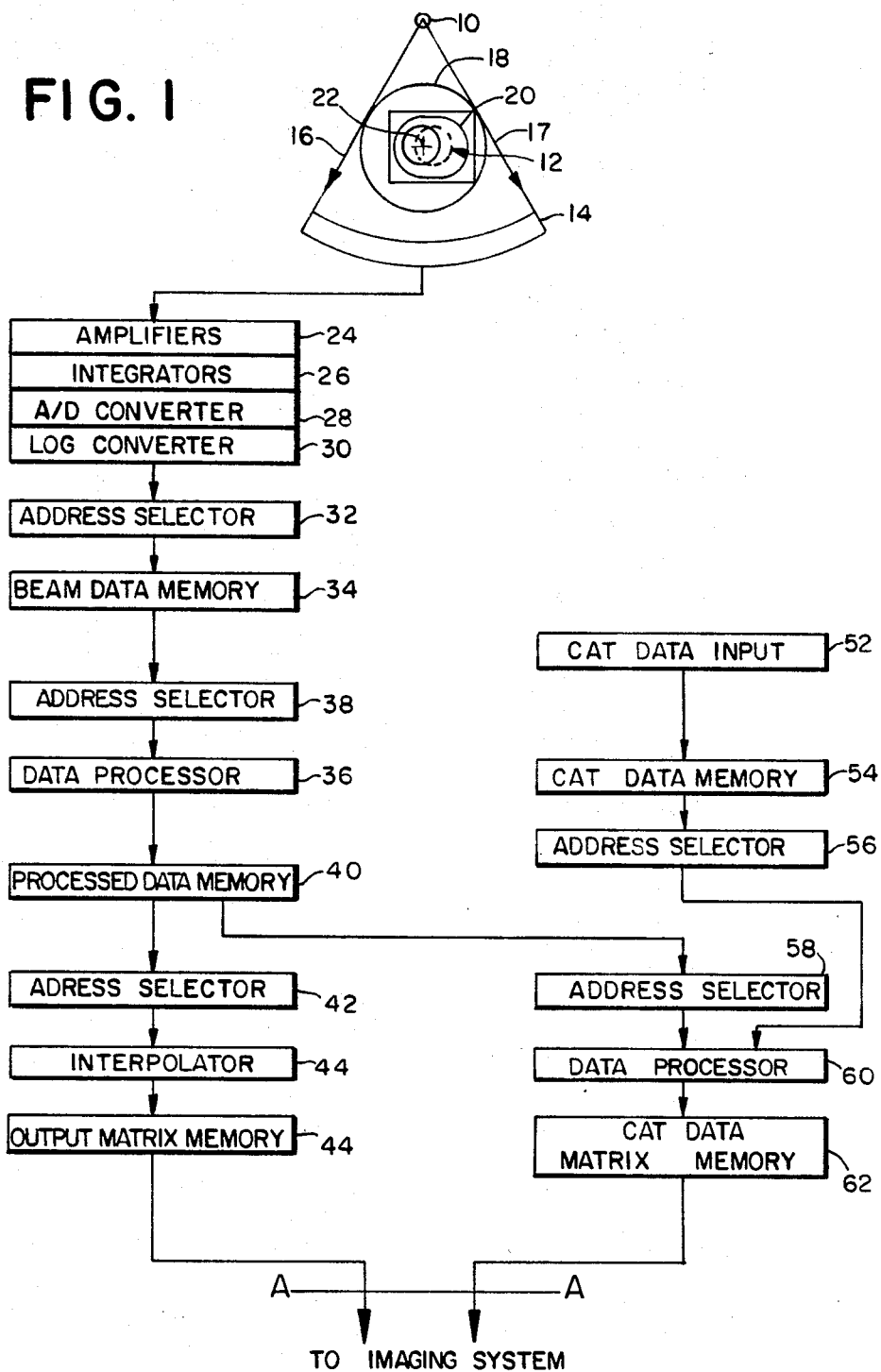
FIG. 1 is a partially schematic, block diagram of a portion of a system representing a preferred embodiment of the invention.

Referring to FIG. 1, a computer-assisted tomographic scanning apparatus hereinafter referred to as a CAT scanning apparatus is shown. The apparatus includes a source 10 of X-radiation which is directed at a portion of a human body 12 shown in dotted lines between the source 10 and a detector 14 of the X-radiation. Lines 16 and 17 depict the extremities of the X-radiation pattern directed from the source 10 to the detector 14. As in the case of the typical CAT scanning apparatus, the source 10 and detector 14 are free to orbit on an axis 22 around a member 18 in which the body 12 is located as supported by a support structure 20.

The output from the detectors 14 are applied to amplifiers 24 and integrators 26 to produce an analog output representing the radiodensity of the body 12 in the scanned region. The analog output is then converted to digital form at an A/D converter 28 prior to conversion to logarithmic form at a log converter 30.

The log converter 30 output is now ready to be stored in memory. This is accomplished by an address selector 32 which selects a particular address in a beam data memory 34.

Figure 2:
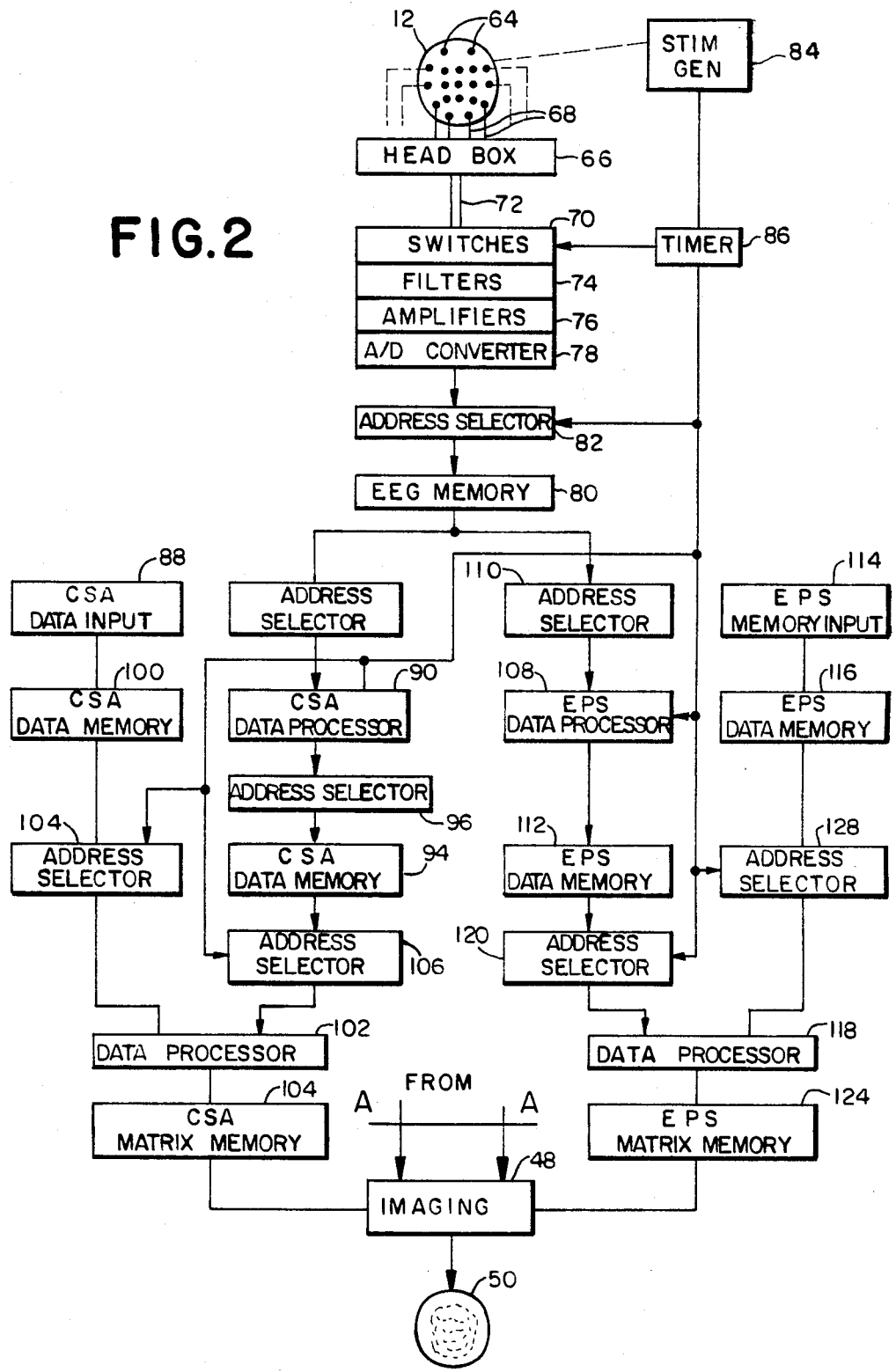
FIG. 2 is a partially schematic, block diagram representing another portion of the system shown in FIG. 1 and interconnected at line A—A.

The contents of the beam data memory 34 are now ready to be processed so as to generate the necessary information in the proper format for the tomographic image. For this purpose, an appropriate address in a data processor 36 is selected by an address selector 38 and the processed data is stored in a processed data memory 40. In order to achieve a high degree of accuracy in image reconstruction, it is necessary to interpolate the data stored in the process data memory 40. This is accomplished by providing an address selector 42 which selects the appropriate address and an interpolator 42 is directly coupled to an output matrix memory 44 for application to the display imaging means 48 as shown in FIG. 2. The output of the imaging means shown in FIG. 2 is a tomographic image 50 which may take the form of a cathode ray tube display or a hard copy photographic image.

The system heretofore described with reference to FIGS. 1 and 2 is described in substantially greater detail in U.S. Pat. No. 3,924,129 and U.S. Pat. No. 4,076,985 which are incorporated herein by reference.

In accordance with this invention, means are provided in the apparatus shown in FIG. 1 for storing and generating data representing a predetermined condition of the body 12, and more specifically, a predetermined condition for a normal body 12. This data stored in memory is then compared with data in the processed data memory representing detected signals from the detector 14 corresponding to the actual condition of the body and various regions thereof.

The stored and generated data representing a predetermined normal condition of the body are obtained by providing a suitable CAT scanning data input 52 as shown in FIG. 1. The input 52 may take the form of a magnetic memory such as a floppy disk which stores in magnetic, digital form signals representing predetermined condition of the various regions of the body under consideration, which conditions are determined by sampling large numbers of bodies. The output from the CAT scanning data input 52 is applied to a CAT scanning data memory having an output coupled to an address selector 56. Another address selector 58 is coupled to the output of the processed data memory 40 representing the actual condition of the body. It will, therefore, be understood that the output signals from the process data memory represent the actual condition of the body at various regions thereof whereas the output signals from the CAT scanning data memory 54 represent a normal predetermined condition at various regions of the body.

The appropriate addresses in a data processor 60 are selected by the address selectors 56 and 58 associated with the CAT scanning data memory 54 and the processed data memory 40 respectively. The data processor 60 provides a comparison function with respect to the signals stored and generated by the CAT scanning data memory 54 and the processed data memory 40 and appropriate data is generated representing the deviation of the detected signals representing the actual condition of the body from the signals representing a normal predetermined condition of the body for various regions of the body. Where a deviation between the actual condition and the predetermined condition exist, the data processor 60 will provide an output signal representing the deviation for any one of the regions of the body in which such a deviation exists. The output signal from the data processor 60 which produces the comparison is applied to the CAT scanning data matrix memory 62 representing deviation from predetermined conditions are applied to the imaging means 48. The CAT scanning image 50 may represent the actual radiodensity as well as indicating a particular region in which the actual radiodensity deviates from a predetermined condition or norm. This will be described in further detail subsequently with reference to FIG. 3.

The invention heretofore described is applicable to CAT scanning of any portion of the body including the central nervous system. An important aspect of the invention which is only applicable in diagnosis with respect to the central nervous system will now be described with reference to FIG. 2.

Referring to FIG. 2, the body 12 comprising a human head is contacted by a multiplicity of electrodes 64 located across the top of the head. The electrode 64 is coupled back to a head box 66 through connections 68, some of which are shown in dotted lines. The purpose of the electrodes 64 and the head box 66 is to couple electrophysiological data from electroencephalagraphic apparatus hereinafter referred to as an EEG apparatus. The apparatus comprises switches 70 coupled directly to the head box 66 through a cable 72, filters 74, amplifiers 76 and an analog-to-digital converter 78.

The output from the A/D converter 78 stores the electrophysiological information in an EEG memory 80 at addresses selected by an address selector 82. The EEG memory is capable of storing signals representing a normal, unstimulated electroencephalographic signal as well as signals generated in response to a stimulus derived from the output of a stimulus generator 84. The stimulus generator 84 is controlled in response to a timer 86 which also controls the position of the switches 70 for connecting various electrodes 64 to the head box 66 as well as the address selector 82 for selecting addresses within the EEG memory 80 corresponding to the particular electrodes 64 which are selected.

The output from the EEG memory 80 is now subjected to computer analysis so as to provide a compressed spectral array hereinafter referred to as CSA. In this connection, an address selector 88 selects an address within a CSA data processor 90 which separates a routine EEG wave form into the various components of various frequencies and amplitude. Signals representing the compressed spectral analysis are then stored in a CSA data memory 94 at addresses selected by an address selector 94.

In accordance with this invention, actual CSA data generated by signals detected from the body 12, more specifically, the central nervous system, are compared with data representing a predetermined CSA condition or norm.

The electrophysiological data in the form CSA data establishing a predetermined condition at various regions of the central nervous system are based on a normal population supplied to the system at CSA data input 98. The CSA data input 98 may comprise suitable magnetic memory such as a magnetic disk which dumps the data into storage in a CSA data memory 100. The CSA data in the memory 100 representing a predetermined condition of the central nervous system and the CSA data in the memory 94 representing the actual condition of the central nervous system is now compared in a data processor 102 after address selection at an address selector 104 and an address selector 106. By comparison in the data processor 102, the deviation between CSA data and the memory 100 and the detected CSA data in the memory 94 is determined and applied to a CSA matrix memory 104 which is coupled to the imaging system 48. The matrix memory 104 is capable of generating a visual overlay on the image 50 representing the deviation of the actual CSA data from the predetermined CSA data representing the norm.

In accordance with another important aspect of the invention, additional electrophysiological information from the EEG memory 80 may be utilized to determine any deviation of the evoked potential spectrum hereinafter referred to as EPS from a predetermined condition representing the norm. This is accomplished utilizing an EPS data processor 108 which receives the actual EPS data from the EEG memory 80 at various addresses selected by an address selector 110. The output fom the EPS processor 108 is applied to an EPS data memory 112.

In order to determine the deviation of the actual EPS data from the norm, an EPS input representing a predetermined or normal EPS condition is applied to an EPS memory input 114 which may take the form of a suitable magnetic memory storage means such as a magnetic disk. The output from the EPS memory input 114 is applied to an EPS data memory 116.

A comparison is now made between the EPS data stored in the memory 112 representing the actual condition of the central nervous system and the EPS data stored in the memory 116 representing a predetermined condition or norm for the central nervous system. The comparison is made in a data processor 118 after appropriate address selections are made by the address selectors 120 and 122. The comparison made in the data processor 118 determines any deviation of the detected actual condition stored in the EPS data memory 112 and the predetermined condition or norm stored in the EPS memory 116. The output from the data processor 118 representing this deviation is supplied to an EPS matrix memory 124.

As noted in the foregoing, a stimulus generator 184 is utilized which is coupled to a timer 86. This assures that the various switches 70 for connecting the electrophysiological signals at the various electrodes 64 are synchronously actuated with respect to this stimulus generator 84. The timer 86 is also required to assure synchronous operation with respect to the processors address selection and memories shown in FIG. 2.

Figure 3:
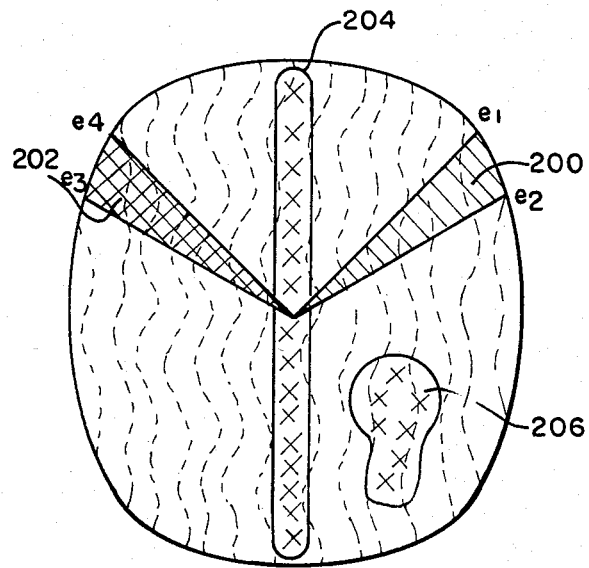
FIG. 3 illustrates a tomographic image with various regions visually indicated in response to the apparatus shown in FIGS. 1 and 2.

It will be appreciated that the image 50 which is displayed is a tomogram representing the radiodensity of the central nervous system. This tomogram may be 3-dimensional or may represent a planar section through the central nervous system as depicted in FIG. 3. As shown in FIG. 3, the various regions have been cross-hatched to indicate deviations of the central nervous system with respect to the norm. As shown in the 2-dimensional tomogram of FIG. 3, the first region 200 has been cross-hatched with a single set of parallel lines. A second region 202 has been cross-hatched with a double set of parallel lines. Regions 204 and 206 have been cross-hatched with "X's." These various cross-hatched regions overlie the basic tomogram.

The particular cross-hatching, as well as the shape of the cross-hatched regions indicate various things to a physician diagnosing the central nervous system utilizing the system of this invention. Both the regions 200 and 202 represent deviation in electrophysiological data derived from the portion of the apparatus shown in FIG. 2. Note the sector-like shape of the regions 200 and 202 which correspond to the area between pairs of electrodes E1–E2 and E3–E4 respectively. These electrodes generally represented by the reference character 64 in FIG. 2 are, of course, positioned at various locations of the head of a patient and the cross-hatched regions 200 and 202 therefore, represent sectors of the central nervous system using information derived when the appropriate switches 70 associated with the electrodes E1 and E2 or E3 and E4 have been closed. In the case of the region 200, the particular cross-hatching is intended to indicate the deviation between the actual CSA data and the predetermined CSA data representing the norm. The region 202 as cross-hatched is intended to indicate a deviation between CSA actual and CSA predetermined or norm as well as a deviation between EPS actual and EPS predetermined or norm. In other words, the cross-hatching with respect to regions 200 and 202 indicate deviation from electrophysiological norms. However, the regions 204 and 206 represent deviation with respect to a radiodensity norm. In particular, the cross-hatched region 204 is intended to indicate a displacement of the midline of the brain. Since the midline of the brain will be indicated on a tomogram by predetermined radiodensity in normal situations, any displacement of the midline will produce a deviation from the norm in radiodensity in the region where the midline should be. The region 206 is intended to indicate a deviation in radiodensity which may, for example, be caused by a tumor in the brain. Actually, the entire brain could be cross-hatched utilizing the cross-hatching of the regions 204 and 206 when the brain is edemas since that would produce an abnormality in radiodensity of the brain.

It will therefore be appreciated that diagnosis of the central nervous system can be greatly aided utilizing the invention. As further examples, hemorrhages may be detected and blood in the cerebral spinal fluid may also be detected. Moreover, the breakdown in the blood/brain barrier may be detected by iondinating the cerebral spinal fluid since this will create deviations in radiodensity of the brain due to the presence of the iodinated CSF in the blood.

It will be appreciated by reference to FIG. 3 that the actual area involved in one of the cross-hatched regions may be readily calculated. For example, it is possible to calculate the area of a ventricle which is enlarged and displayed on the image as shown in FIG. 3, and the CAT DATA matrix memory 62 could in fact be provided with a read-out which provided such a calculation.

A portion of the system shown in FIG. 2 including the head box 66, the switches 70, the filters 74, amplifiers 76 and A/D converter 78 may comprise a Nicholet Med 80 system. Such a system is capable of generating the output from the CSA data processor 90 and the EPS data processor 108.

Although the foregoing specification has described the flow of data through the system, it will be appreciated that various components of the system are receive signals at each input and produce signals at each output. In other words, signals representing the data are generated for each set of data referred to in the foregoing specification.

Although the specification has described a particular embodiment of the invention and modifications have been suggested, it will be appreciated that other embodiments and modifications will occur to those of ordinary skill in the art and such embodiments and modifications will fall within the true spirit and scope of the invention as set forth in the appended claims.

I claim:

1. In a tomographic imaging apparatus comprising X-ray means for scanning a portion of the central nervous system with X-radiation and detecting the X-radiation scanning the central nervous system, processing means for processing detected signals representing the radiodensity of various regions of the scanned body from the X-ray means and imaging means coupled to the processing means for generating an image representing the radiodensity of various regions of the central nervous system, the improvement comprising:

memory means for storing and generating signals representing a predetermined electrophysiological condition of the central nervous system at various regions thereof including the spectrum of components in an electroencephalographic signal;

detector means for detecting signals representing the actual electrophysiological condition of the central nervous systems at various regions thereof including means for spectrally analyzing the components of the detected electroencephalographic signal for the various regions;

comparison means coupled to said memory means and said detector means for comparing the detected signals with the stored signals for said various regions of said central nervous system and generating signals representing the deviation of the detected signals in one of the regions from said stored signals for said one of the regions; and display means coupled to said comparison means and said imaging means for visually indicating said one of the regions representing said deviation on said image.

2. The apparatus of claim 1 wherein said display means comprises means for generating an image of various regions in a plane through said central nervous system, said display means generating a visual overlay of said one of the regions in said plane represented by said image.

3. The apparatus of claim 1 wherein said display means generates a visual overlay of said one of the regions in said image.

4. The apparatus of claim 1 wherein:

said memory means also stores and generates signals representing a predetermined radiodensity for various regions of said central nervous system;

said detector means also detects signals representing the radiodensity of various regions of said central nervous system;

said comparison means coupled to said memory means and said detector means compares the detected radiodensity signals with the radiodensity stored signals and generates signals representing a deviation of the detected radiodensity signals from said stored radiodensity signals for one of the regions; and said display means coupled to said comparison means and said imaging means visually indicates said one of the regions representing said deviation of radiodensity on said image.

5. The apparatus of claim 1 wherein:

said memory means also comprises means for storing signals representing predetermined evoked potentials for various regions of the central nervous system in response to a stimulus; and said detector means also comprises means for detecting electrophysiological signals comprising evoked potentials for various regions in the central nervous system in response to said stimulus.

6. The method of operating a tomographic imaging apparatus comprising X-ray means for scanning portions of the central nervous system with X-radiation and detecting the X-radiation scanning the central nervous system, processing means for processing detecting signals representing the radiodensity of various regions of the scanned body from the X-ray means and imaging means coupled to the processing means for generating an image representing the radiodensity of various regions of the central nervous system, the method comprising:
- storing and generating signals representing a predetermined electrophysiological condition of the central nervous system at various regions thereof including a predetermined spectrum of components in an electroencephalographic signal;
- detecting signals representing the actual electrophysiological condition including an electroencephalographic signal of the central nervous system at various regions thereof including spectrally analyzing the components in the detected electroencephalographic signal;
- comparing the detected signals with the stored signals for various regions of said central nervous system and generating signals representing the deviation of the detected signals in one of the regions from said stored signals for said one of the regions; and
- display means coupled to said comparison means and said imaging means for visually indicating said one of the regions representing said deviation on said image.

7. The method of claim 6 wherein said imaging means comprises means for generating an image of various regions in a plane through said central nervous system and the step of visually indicating comprises generating a visual overlay of said one of the regions in said plane represented by said image.

8. The method of claim 6 wherein the step of visually indicating comprises generating a visual overlay of said one of the regions in said image.

9. The method of claim 6 wherein:
- the step of storing and generating signals comprises storing and generating signals representing a predetermined radiodensity for various regions of said central nervous system; and
- the step of detecting signals comprises the detecting of signals representing the radiodensity of various regions of the central nervous system.

10. The method of claim 6 wherein:
- the step of storing and generating comprises storing and generating signals representing predetermined evoked potentials for various regions of the central nervous system in response to a stimulus; and
- the step of detecting comprises detecting evoked potentials for various regions in the central nervous system in response to a stimulus.

* * * * *